US009008793B1

(12) United States Patent
Cosman, Sr. et al.

(10) Patent No.: US 9,008,793 B1
(45) Date of Patent: Apr. 14, 2015

(54) MULTIPLE ELECTRODE RADIOFREQUENCY GENERATOR

(75) Inventors: Eric R. Cosman, Sr., Belmont, MA (US); Eric R. Cosman, Jr., Belmont, MA (US)

(73) Assignee: Chenes LLC, Belmont, MA (US)

( * ) Notice: Subject to any disclaimer, the term of this patent is extended or adjusted under 35 U.S.C. 154(b) by 1196 days.

(21) Appl. No.: 11/872,447

(22) Filed: Oct. 15, 2007

(51) Int. Cl.
*A61F 2/00* (2006.01)
*A61F 7/12* (2006.01)
*A61B 18/04* (2006.01)
*A61B 18/18* (2006.01)
*A61B 18/12* (2006.01)
*A61N 1/06* (2006.01)
*A61N 1/36* (2006.01)
*A61B 5/0488* (2006.01)
*A61B 5/00* (2006.01)
*A61N 1/40* (2006.01)
*A61B 18/00* (2006.01)
*A61B 18/14* (2006.01)

(52) U.S. Cl.
CPC ....... *A61B 18/12* (2013.01); *A61B 2018/00767* (2013.01); *A61N 1/06* (2013.01); *A61B 2018/126* (2013.01); *A61N 1/36021* (2013.01); *A61B 2018/00761* (2013.01); *A61B 5/0488* (2013.01); *A61B 2018/00434* (2013.01); *A61B 5/4893* (2013.01); *A61B 2018/00714* (2013.01); *A61B 2018/1253* (2013.01); *A61B 2018/124* (2013.01); *A61B 18/1477* (2013.01); *A61N 1/403* (2013.01); *A61B 2018/00654* (2013.01); *A61B 2018/143* (2013.01); *A61B 2018/00839* (2013.01); *A61B 2018/00702* (2013.01); *A61B 2018/00797* (2013.01)

(58) Field of Classification Search
USPC ................ 607/96–102, 115–118; 606/20–50
See application file for complete search history.

(56) References Cited

U.S. PATENT DOCUMENTS

| 4,411,266 | A | * | 10/1983 | Cosman ......................... 606/49 |
| 4,565,200 | A | | 1/1986 | Cosman |
| 4,566,454 | A | | 1/1986 | Mehl et al. |
| 4,597,379 | A | | 7/1986 | Kihn et al. |
| 4,727,874 | A | | 3/1988 | Bowers et al. |

(Continued)

FOREIGN PATENT DOCUMENTS

| WO | WO99/40859 | 8/1999 |
| WO | WO99/40860 | 8/1999 |
| WO | WO00/59394 | 12/2000 |

OTHER PUBLICATIONS

Cosman et al. "Theoretical Aspects of Radiofrequency Lesions in the Dorsal Root Entry Zone," *Neurosurgery*, vol. 15, No. 6, p. 945-950 (1984).

*Primary Examiner* — Joseph Stoklosa
*Assistant Examiner* — Adam Avigan
(74) *Attorney, Agent, or Firm* — Steptoe & Johnson LLP

(57) ABSTRACT

A apparatus for performing tissue modification procedures on a patient's body can include a device, which can be adapted for connection to at least two electrodes, where temperature sensors can be incorporated into tip portions of said electrodes, a high frequency generator, which can be operatively associated with said device, wherein said generator can deliver non-simultaneously a high frequency signal output to each of said electrodes, and a feedback control circuit, which can be configured to regulate the signal output delivery to each of said electrodes so it can maintain a user settable temperature at tip portion of said electrodes when the electrodes can be in contact with the patient's body.

38 Claims, 13 Drawing Sheets

(56) References Cited

U.S. PATENT DOCUMENTS

| | | | | |
|---|---|---|---|---|
| 4,807,620 | A | 2/1989 | Strul et al. | |
| 5,433,739 | A | 7/1995 | Sluijter et al. | |
| 5,571,147 | A | 11/1996 | Sluijter et al. | |
| 5,769,847 | A * | 6/1998 | Panescu et al. | 606/42 |
| 5,951,546 | A | 9/1999 | Lorentzen | |
| 5,983,141 | A | 11/1999 | Sluijter et al. | |
| 6,104,959 | A | 8/2000 | Spertell | |
| 6,161,048 | A | 12/2000 | Sluijter et al. | |
| 6,246,912 | B1 | 6/2001 | Sluijter et al. | |
| 6,259,952 | B1 | 7/2001 | Sluijter et al. | |
| 6,301,506 | B1 | 10/2001 | den Boer et al. | |
| 6,321,120 | B1 | 11/2001 | Surbeck et al. | |
| 6,397,106 | B1 | 5/2002 | DeBrouse | |
| 6,402,739 | B1 | 6/2002 | Neev | |
| 6,428,537 | B1 | 8/2002 | Swanson et al. | |
| 6,440,127 | B2 | 8/2002 | McGovern et al. | |
| 6,447,505 | B2 | 9/2002 | McGovern et al. | |
| 6,482,204 | B1 | 11/2002 | Lax et al. | |
| 6,517,534 | B1 | 2/2003 | McGovern et al. | |
| 6,530,922 | B2 | 3/2003 | Cosman et al. | |
| 6,692,493 | B2 | 2/2004 | McGovern et al. | |
| 6,743,226 | B2 | 6/2004 | Cosman et al. | |
| 6,853,864 | B2 | 2/2005 | Litovitz | |
| 6,869,430 | B2 | 3/2005 | Balbierz et al. | |
| 7,522,953 | B2 * | 4/2009 | Kaula et al. | 600/546 |
| 7,553,309 | B2 * | 6/2009 | Buysse et al. | 606/41 |
| 7,574,257 | B2 * | 8/2009 | Rittman, III | 607/2 |
| 2002/0156472 | A1 * | 10/2002 | Lee et al. | 606/41 |
| 2002/0165531 | A1 | 11/2002 | Goble | |
| 2003/0032951 | A1 * | 2/2003 | Rittman et al. | 606/34 |
| 2003/0212390 | A1 * | 11/2003 | Chen et al. | 606/27 |
| 2007/0032835 | A1 | 2/2007 | Rittman | |
| 2008/0262490 | A1 * | 10/2008 | Williams | 606/34 |

* cited by examiner

MULTIPLE ELECTRODE RADIOFREQUENCY GENERATOR

TECHNICAL FIELD

The invention relates generally to field therapy.

BACKGROUND

The use of radiofrequency (RF) generators and electrodes in neural tissue for the treatment of pain and functional disorders is well known. Included herein by reference, an as an example, the RFG-3C Plus RF Generator of Radionics, Inc., Burlington, Mass., and its associated electrodes are used in the treatment of the nervous system, and the treatment pain and functional disorders. This device is capable of delivering high frequency energy to patient tissue via an adapted electrode, and associated ground or reference electrode. This device is also capable of delivering low frequency stimulation pulses that are used to accurately localize the electrode placement before treatment. This unit delivers high frequency signal output both in a continuous RF mode and in a pulsatory RF mode, referred to as pulsed RF (PRF). In continuous RF mode, target tissue is heated near the uninsulated electrode tip of the high frequency electrode by the application of a high frequency signal output from the RF generator onto the tissue near the uninsulated electrode tip. For example, in continuous RF mode, it is common that a target tissue is heated in the range of 45 to 100° C. to selectively destroy the target tissue by heating. In the pulsed RF mode (PRF), intermittent bursts of high frequency signal output are delivered by the RF generator and applied to target tissue through the uninsulated electrode tip of the high frequency electrode. This is typically used to treat pain syndromes. The PRF signal output typically comprises a short period of on-time of high frequency signal, for example 0.1 to 50 milliseconds of on-time, followed by a period of off-time which has a duration that is substantially longer than the duration of the on-time (for example, 100 to 1000 milliseconds) in which the signal output is substantially lower than the signal output in the on-time burst, for example, near or at 0. The bursts of high frequency signal output are typically in the range of one to five bursts per second, referred to as pulses per second (pps), or Hertz (Hz). Because in PRF in the on-time period, signal output occurs for a short period, the amount of tissue heating near the uninsulated electrode tip of the high frequency electrode is reduced compared to, continuous RF mode for the same magnitude of signal output.

The RFG-3C Plus generator has one electrode output jack for connection to a single active electrode, and it has one reference electrode jack for connection to a reference electrode. When the active electrode is inserted into the body, and the reference electrode is placed, typically on the patient's skin, then RF current form the RF generate flows through the patient's body between the two electrodes. The generator can be activated and its signal output can be applied between the electrodes. Typically, this is referred to as a monopolar configuration because the active electrode is of smaller area than the reference electrode, and so the concentration of RF current is highest near it and the action of the RF electric field, whether for heating or for pulsed RF field therapy is greater there. This usually referred to as a single electrode configuration since there is only one "active" electrode.

Parameters that can be measured by the RFG-3C Plus RF generator include impedance, HF voltage, HF current, HF power, and electrode tip temperature. Parameters that may be set by the user include time of energy delivery, desired electrode temperature, stimulation frequencies and durations, and level of stimulation output. In general, electrode temperature is a parameter that may be controlled by the regulation of high frequency output power. Existing RF generators have interfaces that allow the selection of one or more of these treatment parameters, as well as various methods to display the parameters mentioned above.

In another example, the reference electrode can be inserted into the patient's body, and it can have an active area that is smaller and of comparable size to the active electrode. In that case, both electrodes become "active" in the sense that both of the have high temperature or electrical field effects on the tissues around them, so that they are both involved actively in the therapeutic effects the RF signal output. This can be referenced to as a single "bipolar" configuration.

A limitation for the monopolar and the bipolar configuration just described is that it limits the RF therapy to one or two electrode locations, respectively. In some situations it is desirable to treat more than one or two positions in the bodily tissue, and thus desirable to have more electrodes involved as the procedure goes on. For example, this can save time if there are multiple sites to be treated, as for example, multiple levels of the spinal medial branches to be treated for back pain.

The Untied Stated patent application Publication entitled Method and Apparatus for Diagnosing and Treating Neural Dysfunction, by W. J. Rittman, Pub. No. US 2007/0032835 A1, Pub. Date: Feb. 8, 2007, describes an RF generator system comprising an RF generator with multiple active electrode output connections that enables the RF signal output the generator to be connected and delivered simultaneously to more than one electrode to deliver a therapeutic effect at each of the electrode positions at the same time. The RF generator's signal output is switched by switches and switch controllers so that the RF generator's output is applied to multiple electrodes at the same time, that is, simultaneously. In another aspect, the RF generator's switches and switch controllers are independent, that is the switch and switch controller for one of the electrodes performs independently from those of a second electrode or from those of multiple individual electrodes. This has one disadvantage that, because the signal output can be applied to more than one electrode at the same time, the voltage of the generator's power supply and output electronics can be loaded down at the same time, causing sag or droop of the signal output voltage during application. Another disadvantage is that the electrical field from each of the electrodes adds coherently in the bodily tissue, making it more difficult to separate their individual effects on the bodily tissue. Another disadvantage is that it makes it more difficult to control the RF signal output and to maintain the RF signal output so as to maintain the temperatures of the electrodes at a set temperature chosen by the user.

Examples of high frequency generators and electrodes are given in the papers of entitled "Theoretical Aspects of Radiofrequency Lesions and the Dorsal Root Entry Zone," by Cosman, E. R., et al., *Neurosurgery* 15:945-950, 1984; and "Methods of Making Nervous System Lesions," by Cosman, E. R. and Cosman, B. J. in Wilkins R. H., Rengachary S. S. (eds): *Neurosurgery*, New York, McGraw-Hill, Vol. III, pp. 2490-2498, 1984, and are hereby incorporated by reference herein in their entirety.

Four patents have issued on PRF by Sluijter M. E., Rittman W. J., and Cosman E. R. They are "Method and Apparatus for Altering Neural Tissue Function," U.S. Pat. No. 5,983,141, issued Nov. 9, 1999; "Method and System for Neural Tissue Modification," U.S. Pat. No. 6,161,048, issued Dec. 12, 2000; "Modulated High Frequency Tissue Modification," U.S. Pat. No. 6,246,912 B1, issued Jun. 12, 2001; and "Method and Apparatus for Altering Neural Tissue Function," U.S. Pat. No.

6,259,952 B1, issued Jul. 10, 2001. These four patents are hereby incorporated by reference herein in their entirety.

In one example of the use of RF generators, a patient may complain of back pain, or some other pain of known or neuropathic origin. A clinician will often perform diagnostic blocks with local anesthetic by injecting the anesthetic into the areas that are suspected of generating the pain. If the patient receives temporary pain relief from these injections, the doctor concludes that the anatomical positions of the origin sites of the pain are in the locations where he made these injections. Unfortunately, the origin of pain is poorly understood; perceived pain at a certain level in the back, for instance, can actually be created from many different and multiple sources and anatomical locations.

Once a location has been identified, the clinician will decide to deliver high frequency signal output form a high frequency generator to this location to permanently destroy the source of the pain. A ground or reference plate will be placed on the patient's thigh to provide a return path for the high frequency energy. An insulated electrode with a small uninsulated tip will be placed at the expected target location. Stimulation pulses will be delivered at a sensory frequency (typically 50 Hz), and a stimulation voltage signal output will be applied to the electrode. The clinician is looking for a very low threshold of response from the patient (e.g., less than 0.5 V) to ensure that the electrode is close to the sensory nerves. They will then perform a stimulation test at a muscle motor frequency (e.g., 2 Hz), and increase the stimulation voltage output to 2 volts. In this instance, they are looking for no motor response in the patient's extremities as this would indicate the electrode was too close to the motor nerves. Treatment in this area could cause paralysis. Upon successful completion of these tests, high frequency energy is typically delivered for one or more minutes, while maintaining an electrode tip temperature between 70 and 90 degrees. Alternatively, high frequency signal output can be delivered for one or more minutes, but in a pulsed mode where the high frequency signal output is on for a short period of on-time and off for a long period of off-time, and thus the pulsed high frequency application will not produce any appreciable heating (reference is made to sited patents in the Background section herein)

Although these treatments are successful, they have several drawbacks. In practice, most patients need treatments at several different nerve locations. This requires placing the electrode, performing the stimulation, and delivering the high frequency signal output at each location, and then repeating the process. This can cause a great deal of wasted time, and patient discomfort, while waiting for the high frequency signal output to be delivered. Another drawback is that, in spite of successful stimulation testing; the target nerve is often not destroyed, thus resulting in no decrease of pain. The clinician is left to determine whether the target nerve has been missed, or whether the pain generator is located elsewhere in the body.

SUMMARY

The present invention relates generally to the applications of RF to multiple electrodes positioned in tissue of the living body. In one example, an RF generator has connections to more that one electrode so that therapeutic effects can be delivered to multiple sites on the living body during the same treatment session. An RF power source in the RF generator connects to the individual electrodes through switches and controllers in a way that the signal output of the RF generate is delivered non-simultaneously to the electrodes. In one example, the switches and the controllers for the individual electrodes are dependent on each other to assure, for example, that the signal output of the power source is only connected to one electrode at a time. In another example, the controllers and switches are made dependent so that the signal output of the generator is only connected to bipolar pairs of the multiple electrodes at separate times, that is, non-simultaneously. One advantage of this non-simultaneous connection to the individual electrodes is that the signal output, for example, the voltage of the power source, is only being delivered to one electrode at a time, and thus the power source will not be over-loaded and thus its signal output will not be pulled down or sag. Another advantage is that, in one example, since only one electrode is activated at a time, the therapeutic agent, for example, heat or the electrical field is applied to the target tissue separately in time slices. This has an advantage that that the circuit controls for each electrode can be operated separately in time from the circuit controllers of the other electrodes. This has one advantage of simplifying the control algorithm for overall control of the heating and overall time of the treatment of the procedure. The generator can deliver programmatically the high frequency signal output to each of said electrodes and/or the generator can deliver sequentially the high frequency signal output to each of said electrodes.

In one example, the signal output of the RF generate is applied non-simultaneously in a cyclical time sequence that is controlled by a master timing controller in the RF generator. One advantage of that is the signal is applied in a smooth time sequence. The time space can be divided into time bins or time slices, each time slice being devoted to one electrode, and the time slices repeat themselves in cyclical manner. The electrode controllers synchronize the series of these time slices and thus synchronize the delivery of the high frequency signal output application to the multiple electrodes. One advantage of this is that the control algorithm is separable in terms of the temperature and the time bin slice for an individual electrode, making the entire control of the multi-electrode application linear and separable in time.

In one example, the dependent controllers are synchronized with a common clock. During the on-time time slice for an individual electrode, its controller will apply an amount of signal output, for example, voltage, on that electrode with sufficient amplitude, has governed by the controller, to elevate the temperature or the electrical field at that electrode. In one example, the controller can be connected to a temperature sensor in the electrode so that the signal output level delivered to the electrode as governed by the controller, is determined by comparison of the measured temperature at the temperature sensor to a set temperature decided upon or, in one example, by the operator. In another example, during the time slice of one electrode, the signal output level applied to the electrode can be delivered to the electrode for a variable fractional time during the time slice, so that the controller can drive, for example, the temperature or the electric field at the electrode towards or away from some target or set value or, in another example, towards a set value that has been pre-set by the user or which is derived by a feed-back algorithm programmed into the controller.

In another example, the time slices relate to individual pairs of electrodes that are to be used in a bipolar configuration. Bipolar pairs are activated during non-simultaneous times and by dependent, coordinated controllers. One advantage of this is that bipolar pairs of electrode can be activated separately and without coherent interference from another pair of bipolar electrode pairs.

Disadvantages of the prior art are overcome by the present method and system which relate to delivering the signal output from a high frequency generator non-simultaneously to more than one treatment electrode that are involved in the clinical procedure. In one example, the high frequency signal output is cyclically sequenced to the multiple electrodes so that no two electrodes have the high frequency signal output applied to them at the same time, and the signal outputs to each electrode are regulated by a feedback mechanism included in the system such that each electrode's tip temperature is maintained to a level (set temperature) set by the user. This greatly reduces treatment time, providing the patient with a shorter period of discomfort as well as not wasting valuable clinician and procedure-room time.

In one example, EMG measurements are displayed on the system to allow the clinician to determine whether the target nerve has been destroyed, as well as the display of pre-treatment and post-treatment sensory stimulation thresholds to measure the degree of desensitization of the target nerve. Measuring the EMG signals allows the clinician to determine whether the target nerve has been successfully treated. Comparison of pre-treatment and post-treatment sensory stimulation thresholds gives the clinician an immediate look at the desensitization of the target nerve.

In one example, the system can deliver at different times in the procedure, both high frequency signal output as well as low frequency stimulation pulses. The device can be, in turn, connected to greater than one treatment electrode. These electrodes have temperature sensors attached to their tips, which reports the tip temperature of each electrode to the system. The system has a user interface which allows the signal output from the system, in one mode, to be connected independently and/or individually to each of the multiple electrodes, and also, in another mode, to enable the high frequency signal output from the system to be connected in sequenced, non-simultaneous time-cycles to the multiple electrodes that are connected by cables to the system. In this way, the low-frequency stimulation signal output from the system can, in one phase of the procedure, be independently connected to each of the patient electrodes. Then, in another phase of the procedure, the high frequency signal output from the system can be connected non-simultaneously, and in a sequential manner that is controlled by the system, to the multiple electrodes. Temperature regulation of the temperature measured at the multiple electrodes can be controlled by the system during the time that the high frequency signal output is being applied in the heating phase of the procedure. The system can provide the capability of both sensory and motor stimulation testing, as well as impedance monitoring to be performed on each of the multiple electrodes during the procedure. When it is desired that the therapeutic high frequency signal output is to be delivered, the user interface allows the non-simultaneous, sequential connection the multiple electrodes to be carried out by the system control electronics and feedback algorithms. Tip temperatures from each of the multiple electrodes can be readout and stored in the system, and a set temperature for each electrode can be chosen by the user. The device can continually compare each of the temperatures from the electrodes to the set temperature. If the electrode tip temperature for an individual electrode exceeds the set temperature, the high frequency signal output to that electrode can be reduced during the programmed time slice of activation of the high frequency signal output to that electrode Similarly, if the electrode tip temperature is less than the set temperature, the high frequency signal output to that electrode can be increased by the system control electronics.

In one example, a system graphic display, which allows EMG and/or EEG signals to be recorded and displayed. In another example, speaker and/or a headphone output allow the EMG and/or EEG signals to be audibly detected and analyzed.

In one example, the present system and method can comprise a high frequency power source that is integrally built into the system. In another example, the system can comprise a stand-alone peripheral device that can be connected between a high frequency power source and the multiple electrodes.

In one example, the system and method of the present invention can be applied to the nervous system for the treatment of pain and/or functional neurological diseases such as Parkinson's disease or mood disorders. In another example, the system and method can be applied to treat cancerous tumors or other functional disorders anywhere in the patient's body.

The details of one or more embodiments of the invention are set forth in the accompanying drawings and the description below. Other features, objects, and advantages of the invention will be apparent from the description and drawings, and from the Claims.

DESCRIPTION OF DRAWINGS

In the drawings that constitute part of the specification, embodiments exhibiting various forms and features hereof are set forth, specifically.

DETAILED DESCRIPTION

Figure 1:
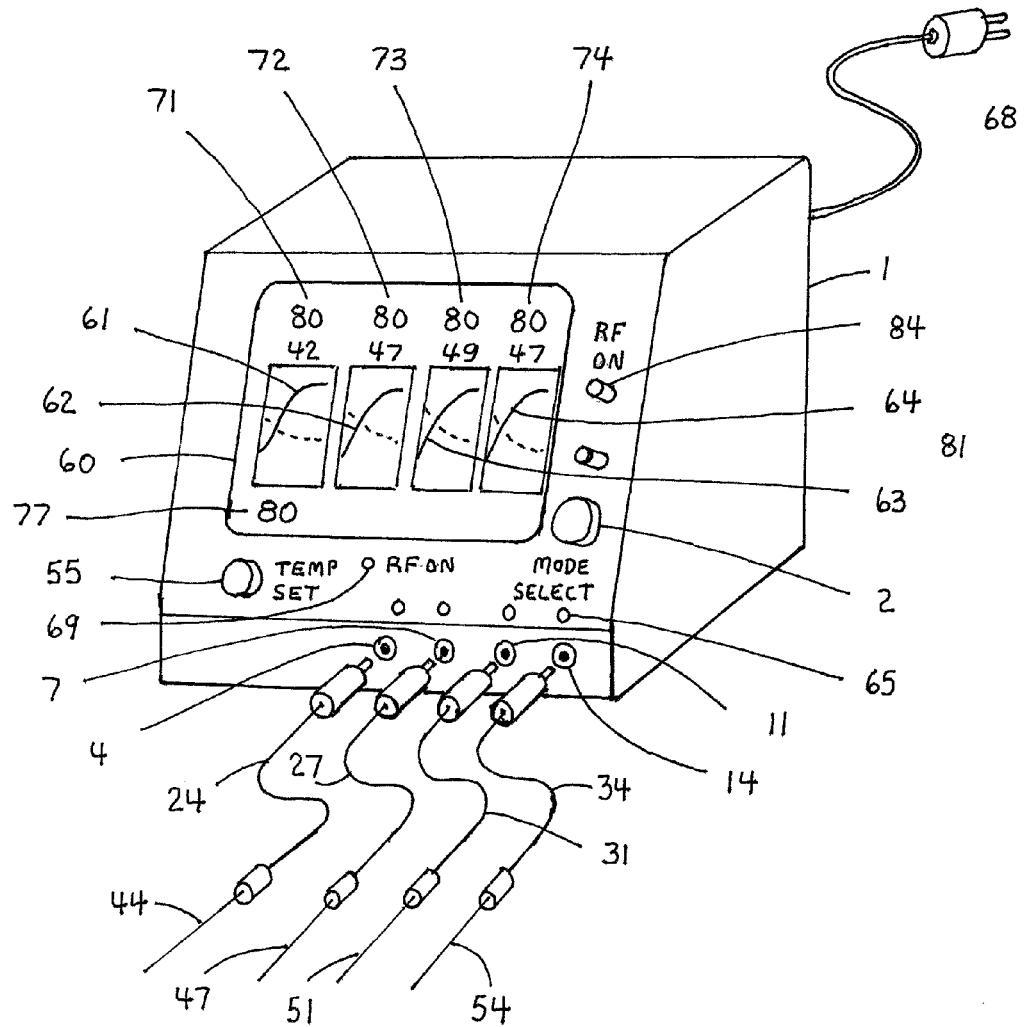
FIG. 1 is a schematic diagram showing a high frequency generator with four electrodes connected to it and a graphic display.

Referring to FIG. 1, an RF generator 1 that can be connected to multiple electrodes is shown. Signal output from the generator can connect to output jacks 4, 7, 11, and 14. Electrodes 44, 47, 52, and 54 can be connected to the output jacks by cables 24, 27, 31, and 34, respectively. Mode select switch 2 allows the user to switch between an individual output mode of the generator 1 wherein signal output from the generator 1 is connected to individual electrodes, one at a time, or to a multiple output mode wherein signal output from the generator 1 is connected in a cyclical, non-simultaneous sequence to multiple electrodes 44, 47, 51, and 54. The individual mode permits the RF generator signal outputs to selectively be connected to each electrode individually for the purpose of doing individual impedance measurements, stimulation threshold testing, EEG or EMG recording, or individual electrode RF lesion making. The multiple out mode of the mode select switch allows therapeutic high frequency signal output from the generator 1 to be delivered to the electrodes 44, 47, 51, and 54 in a cyclical sequence that is automatically programmed into the generator 1, so that the high frequency energy is delivered in a sequential and non-simultaneously time pattern to the multiple electrodes.

The individual electrode temperatures can be measured either in a sequential or in a continuously time pattern and the measured temperatures can be compared to the user set temperature, represented by the display 77 and set by the knob 55 in FIG. 1. For example, in this embodiment the individual electrode temperatures are displayed on a two-dimensional graphics panel identified by 60 in the figure. Also within the graphics display is a representation of temperature versus time displayed in graphic format, for example, as line graphs 61, 62, 63, and 64 in FIG. 1. Indicator lights, represented, for example, by 65 in FIG. 1, indicates which electrode or which set of electrodes is being used in the procedure. In this way the user always knows which electrode is intended to be active or is activated when the mode select 2 has been set to a particular electrode or set of electrodes, and will also indicate during high frequency therapeutic treatment which electrodes are being involved in the procedure according to the system and method described herein.

Referring to FIG. 1, in one example, the high frequency power source or high frequency generator that delivers the high frequency signal output and/or low frequency stimulation signal output pulses could be incorporated into the apparatus 1, or could be a separate stand-alone unit, with the apparatus 1 being interposed between the high frequency power source and the electrodes. In one example, as illustrated in FIG. 1, an AC line 68 can connect the apparatus 1 to an electrical outlet supply power for the apparatus 1. In another example, apparatus 1 can be a battery-operated device wherein the power is supplied by a battery (not shown) that can make the apparatus 1 portable.

The mode selection 2 can be implemented in many ways, for example, knobs, pushbuttons, remote control voice control, or other means. In one example, the features of the user interface of apparatus 1 could be achieved with or without displays such as 60, and, in one example, can use up/down pushbuttons rather than rotatable selector knobs to select or advance or decrease control levels. In one example, the mode select 2 can connect each electrode individually to the high frequency power source, and can also have another position which connects each electrode independently to an EMG or EEG measuring circuit, where the EMG or EEG signal can be displayed on a two-dimensional graphics display. In one example, an additional position on the mode select 2 can deliver high frequency signal output comprising either, (a) in one mode, continuous trains of high frequency signal waves, or (b) in another mode, trains of pulsed high frequency signal bursts. In one mode, for example, these modes of high frequency signal output can be delivered by a programmed cyclical sequence non-simultaneously to multiple electrodes that have been selected by the user to be active during the procedure. In one example, a feedback circuit can be incorporated into apparatus 1 which is adapted to maintain each electrode tip at a temperature equal to a set temperature, for example, a value set by the by control 55 and displayed, as for example, by the digital display 77.

In other possible ergonomic embodiments of this invention, additional displays, buttons, and/or indicators can be included to allow and/or assist the operator in controlling the device. For example, in FIG. 1 an RF 'ON' indicator light, represented by 69, can indicate when high frequency signal output is being delivered to electrode outputs.

Figure 2:
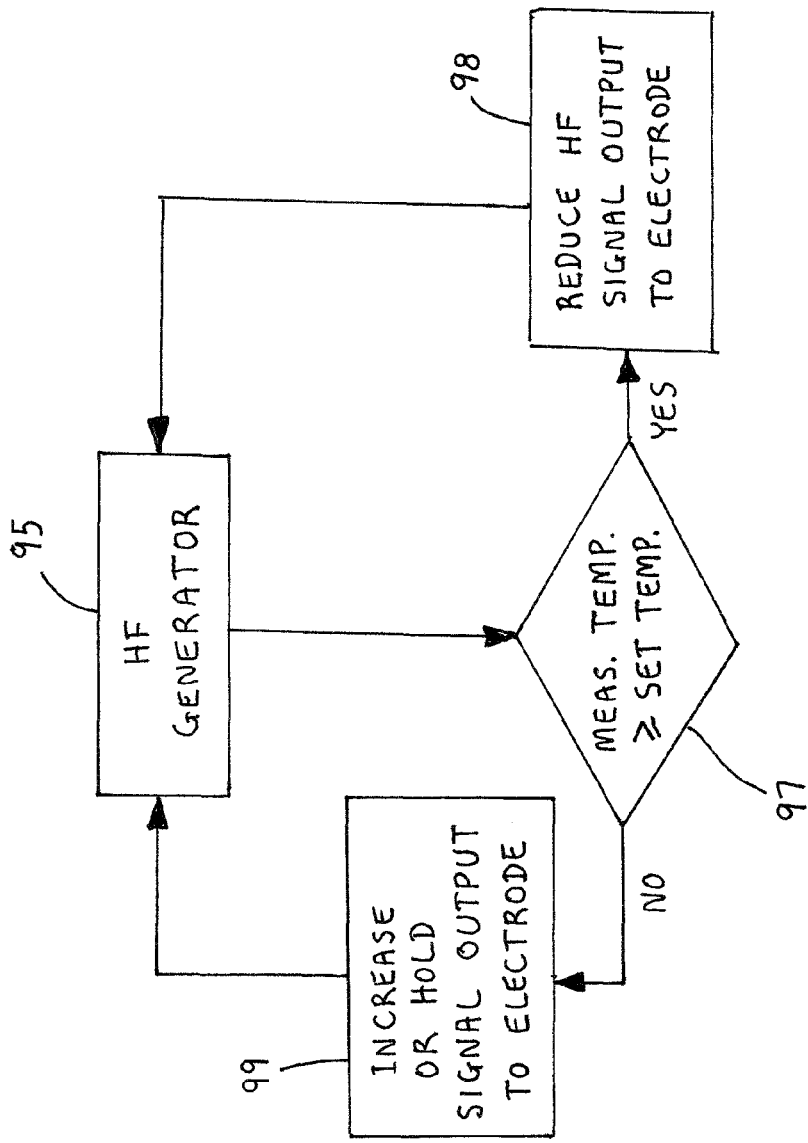
FIG. 2 is a schematic diagram showing feedback and control circuitry.

Referring to FIG. 2, in one example, a logic control diagram shows a basic feedback mechanism for each of the temperature controlled electrodes that are connected to the apparatus such as 1 in FIG. 1. High frequency power supply 95 delivers high frequency signal output. The temperature of the electrode receiving this high frequency signal output, as measured by a temperature sensor in the electrode, and the user selected set temperature, are delivered to a logic circuit decision-making element, and represented by 97. If the electrode temperature is greater than the user set temperature, the high frequency power or signal output to that electrode is reduced or turned off. This action is represented by block 98. Then this process starts all over again, where the electrode temperature is once again compared to the user set temperature. Conversely, if the measured temperature for that particular electrode is less than the user set temperature the high frequency signal output remains on or increased, and the electrode temperature is subsequently compared to the user set temperature. In this way temperature feedback is realized, which will maintain the electrode temperature at the same level as the user set temperature.

Figure 3:
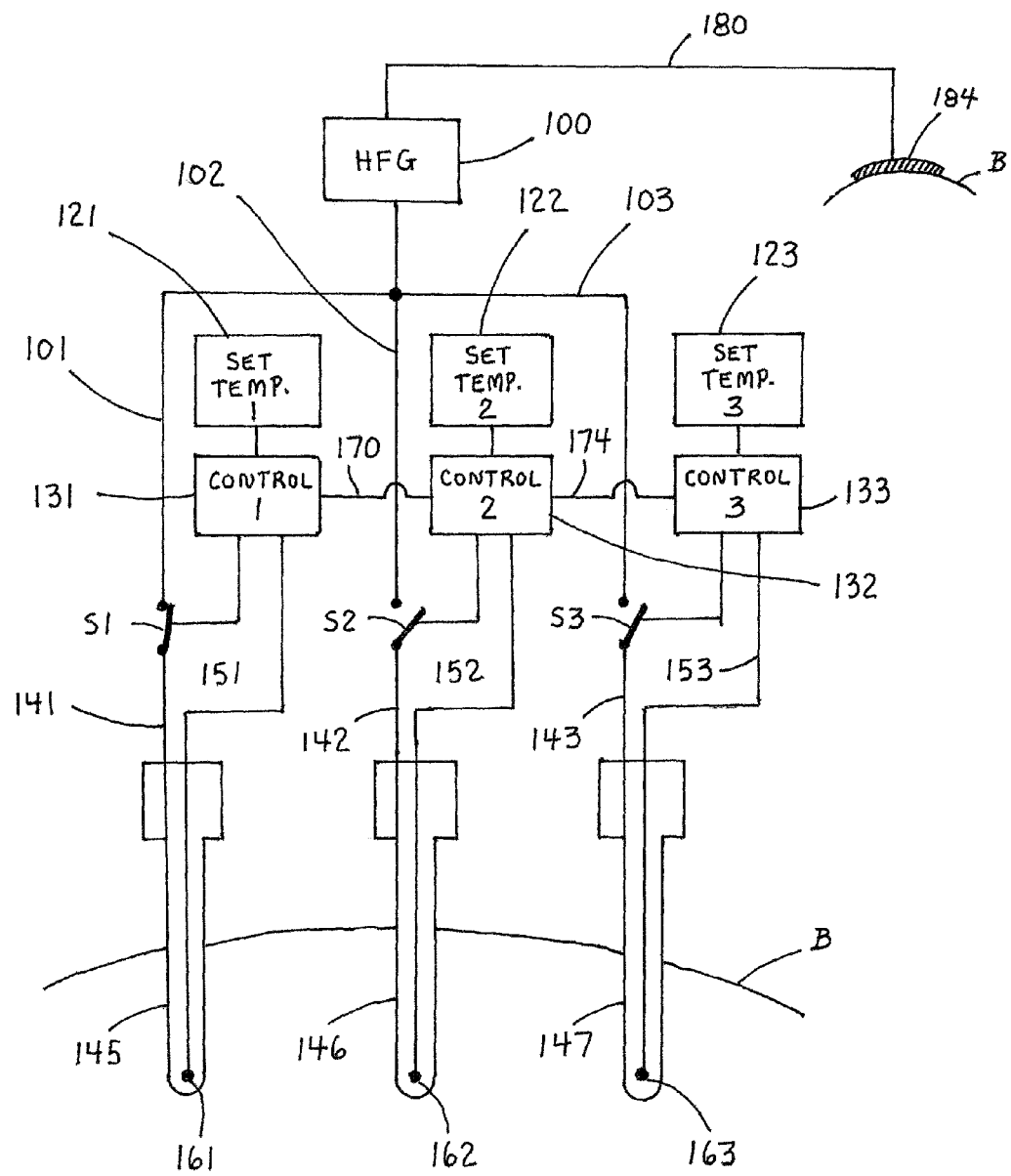
FIG. 3 is a schematic diagram showing a circuit block elements for dependent control of three electrodes connection to a high frequency generator with non-simultaneous energizing of the electrodes.

Referring to FIG. 3, a schematic diagram is shown, in one example, of a feedback and control system involving the use of multiple high frequency electrodes. The system is configured and controlled so that the electrodes 145, 146 147. The electrodes are connected to the system, and they are in contact to the patient's body B. The electrodes receive the signal output from the high frequency generator supply 100 in a non-simultaneous sequence, so that an individual electrode receives power from the high frequency power source during a time slice during which the other electrodes do not receive the high frequency power. For example, in FIG. 3, there are three electrodes 145, 146, and 147 that have cable connections 141, 142, and 143, respectively, to the system. These connections connect to switches S1, S2, and S3, respectively, that connect further through connections 101, 102, and 103, respectively, to the high frequency generator 100 that supplies the high frequency signal output that energizes the electrodes. In one example, as illustrated in FIG. 3, the switch S1 is closed in the time slice corresponding to the state of the system shown in FIG. 3, and at this same time slice the switches S2 and S3 are both open. Thus in the time slice of FIG. 3, only the electrode 145 can be activated or connected to the signal output of the high frequency generator 100. This condition that S1 is closed is controlled by the controller 131. Controller 131 is connected logically to controller 132 and to controller 133, that control the state electrode of switches S2 and S3, respectively, by the connections 170 and 174. In one example, the controllers 131, 132, and 133 are logically linked so that only one of the switches S1, S2, or S3 can be closed at any given time. This means that the electrodes cannot be energized by the signal output of the high frequency generate 100 at the same time; that is they are energized non-simultaneously. For example, at another time, S2 can be closed, and S1 and S3 must be open. At another time, S3 is closed, and S1 and S2 must be open. In one example, the controllers 131, 132, and 133 can be cyclically synchronized by a common clock signal so that they close and open the switches automatically in time slices that repeat according to programmed cycle built into the controllers. The common clock or the common synchronizer can be a separate element (not shown) or can be clocks built into one or more of the controllers 131, 132, or 133. In one example, the controllers 131, 132, and 133 are cyclically activated so that the electrodes are allotted specific repeatedly cycled time slices in which they are connected non-simultaneous to the high frequency generator. During an electrode's allotted time slice, for example, for electrode 1, the controller for that electrode, for example, controller 131 for electrode 145, will controller the amplitude or the dwell time of the signal output from 100 so that the power on electrode 145 will be such as to drive the temperature, measured by the temperature sensor 161, toward the set temperature for electrode 145 as set on 121. This is a feedback control on temperature for electrode 1 that can be carried out by the controller 131.

Referring to FIG. 3, each of the electrodes has a temperature sensor built into them indicates by the elements 161, 162, and 163, corresponds to electrodes 145, 146, and 147, respectively. For example, the temperature sensors can be TC thermocouple sensors that are commonly used in RF electrodes. The temperature signal can be fed into the controllers by the connections 151, 152, and 153, respectively. In one example, there can be a set temperature control, illustrated by the elements 121, 122, and 123, whereby the user can set a temperature which the respective electrodes should lock onto during the procedure. As an illustration of how the circuit can function, electrode 145 can be chosen, as an example, during the time slot for which it is energized. The same descriptions can apply to electrode 146 and electrode 147 during their respective time cycles. Temperature sensor 161 is incorporated into electrode 145 that reports the temperature at the tip electrode 145. The high frequency power connection 141 connects to the electrode 145 that in turn connects to the tissue around electrode 145 in the patient's body B. The high frequency power thus passing into the tissue heats the tissue, and, in turn, heats up the electrode 145 and the temperature sensor 161 within it. Temperature measured by 161 is reported via 151 to controller 131. Control 131 also has an input signal from set temperature control 121, and compares the set temperature to the measured temperature from 161 to determine how long switch S1 should be closed and when it should be opened during the allotted time slice for electrode 145. In this way, the electrode temperature can converge to the set temperature. Switch S1 is shown as a generic switch, and can comprise electrical, mechanically and/or optically switching technology. The high frequency power source 100 is connected and disconnected to electrode 145 via switch S1 and the opening and closing of S1 is modulated, in one example, via controller 131. Controller 131 compares the user set temperature from 121 to the reported electrode tip temperature from sensor 161 and determines the delivery of the signal output from supply 100 to electrode 145. This is an example of a feedback circuit is established to maintain the temperature of electrode 145 at the user set temperature. A similar feedback control for electrodes 146 and 147 can be done during their respective on-time slots. In this way, the electrodes can be energized by the high frequency power source in a non-simultaneous manner, and the temperature on the multiple electrodes can be controller according to chosen set temperatures in a relatively continuous manner during the clinical procedure. The procedure carried out by the illustrative circuit of FIG. 3 can be done for other numbers of high frequency electrode, for example, two, or four, or any number of electrodes.

Figure 4:
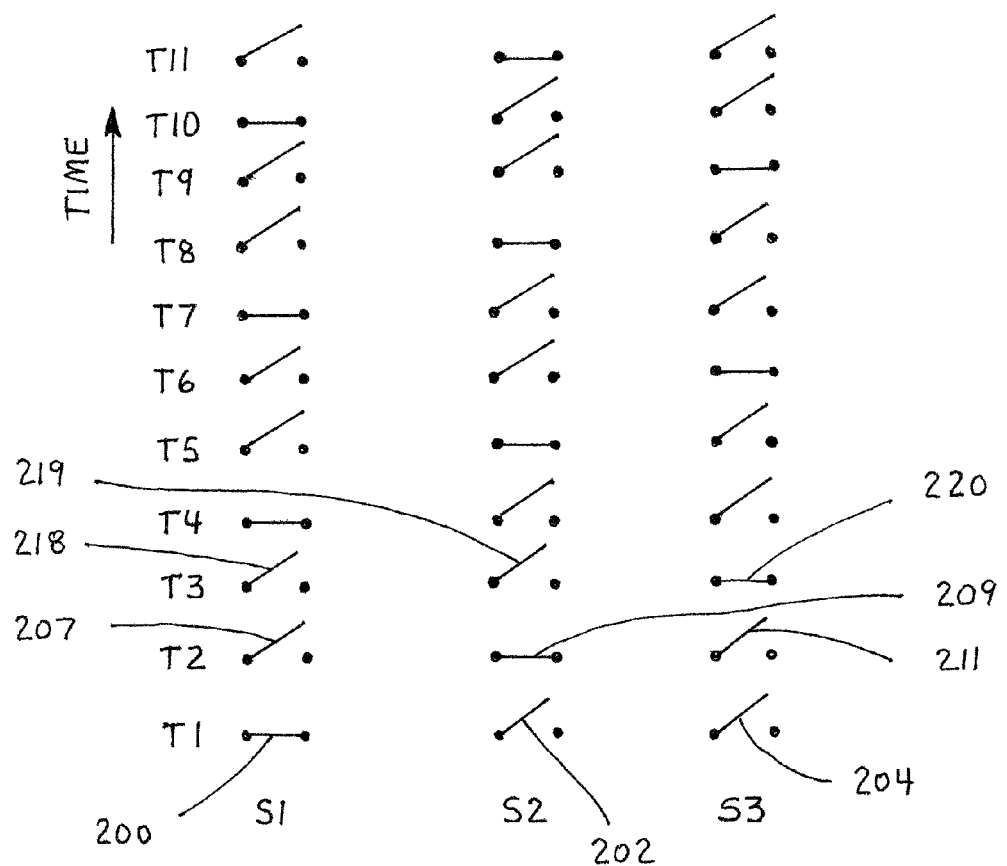
FIG. 4 shows a schematic diagram of time slices with non-simultaneous sequencing of electrode activation with respect to a high frequency generator.

Referring to FIG. 4, a sequence of time slices T1, T2, T3, T4, . . . etc are indicated on the vertical axis, and the state of the switches, as for example, the switches S1, S2, and S3 in FIG. 3, are shown schematically in configuration of open and closed states. For example, in time slice T1, switch S1 is shown in a horizontal position 200, meaning that it is closed, and switches S2 and S3 are shown in an open state indicated by the inclined angle of the schematic switch arms 202 and 204, respectively. This would be the condition in which the signal output from the high frequency generator is delivered to electrode associated with S1, as for example, the electrode 145 in FIG. 3. This state can be controlled by the controllers, for example, shown in FIG. 3. In the next time slice T2, S1 is open indicated by 207, S2 is close indicated by 209, and S3 is open indicated by 211. This corresponds to the signal output being delivered the electrode 146 in FIG. 3, but in that time slice T2, no signal output is being connected to the electrodes 145 and 147. In the next time slice, T3, S3 is closed indicated by 214, and switches S1 and S2 are open indicated by 218 and 219, respectively, so that the electrode 147 in FIG. 3 is activated, and the other electrodes 145 and 146 are not. This cycle of switches being opened and closed in successive time slices continues as shown in FIG. 4. In one example, the length of time of the time slices can be controlled by the controllers as for example, 131, 132, and 133 in FIG. 3. The dwell time of signal output on a particular electrode in a particular time slice can be modulated by the controllers according to the measured temperature of the electrodes and the feedback control circuit as describes with respect to the FIGS. 1, 2, and 3.

Figure 5:
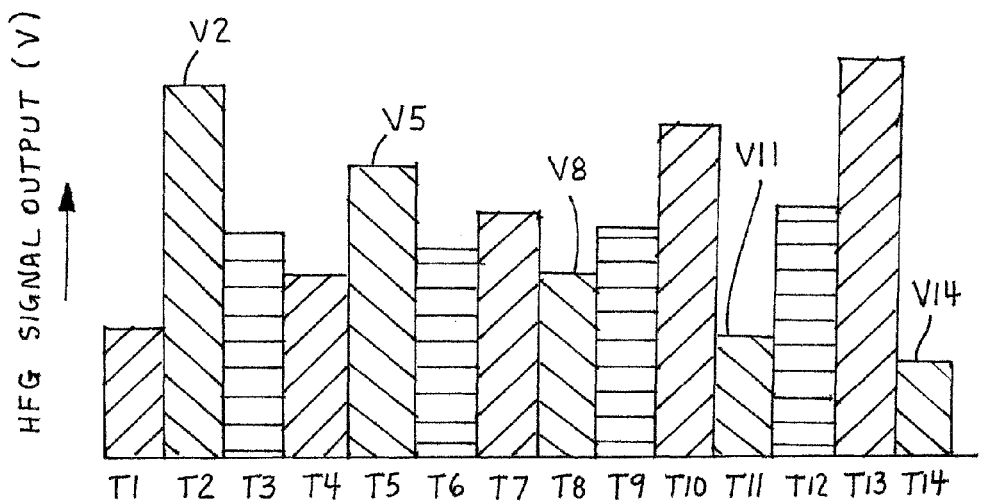
FIG. 5 shows a schematic diagram of cyclical sequencing of time slices of electrode energizing with signal output amplitude variations to enable feedback control of the high frequency therapy.

Referring to FIG. 5, in one example, the signal output level V of the high frequency generator is displayed schematically on the vertical axis, and the time slices T1, T2, T3, etc are shown schematically on the horizontal axis. As in the previous figures, the time slices can correspond to the non-simultaneous time slots for the opening of the electrodes. In one example, the time slots can be of equal duration. For example, if the time to cycle through all of the electrodes is one second, then the individual time slices for each electrode can have ⅓-second durations. The time slices T1, T4, T7, etc can corresponds to signal output connection to electrode 145 of FIG. 1; T2, T5, T8, etc can corresponds to electrode 146; and T3, T6, T9, etc can corresponds to electrode 147. During each time slice, the controllers, as for example 131, 132, and 133 in FIG. 3, can deliver the appropriate level of signal output V to the corresponding electrode, whereby, for example, the temperature of the electrode can be chosen at the set temperature. In one example, the level of electrode 146 corresponding to T2 is held at the value V2, then at slice T5 it is held at V5, and at T8 at level V8, and so on, these values being chosen or governed by the controller of the electrode 146 so that the temperature measured at the electrode can be held at a desired level. The same electrode prescription can apply for the other electrodes and their times slice. One advantage is that because the time slices and the signal output are non-simultaneously applied, the controllers that are synchronized to discriminate the time slices can individually feedback control each electrode separately during their respective time slices. Another advantage is that since the signal output is non-simultaneously applied, the high frequency power supply is not loaded down during each time slice with more than one electrode, so that it can better maintain it source signal output levels.

Figure 6:
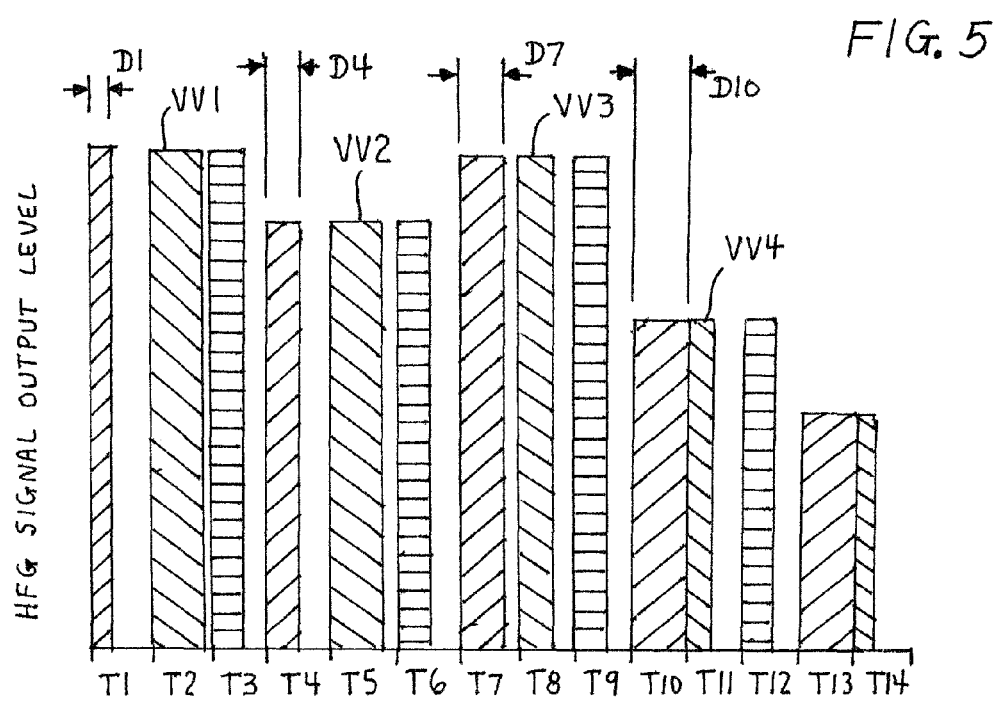
FIG. 6 shows a schematic diagram of time-bin slices that are cyclically sequenced so that the multiple electrodes are energized separately in time, and the magnitude of the heating effect for a given electrode is modulated by varying the percent of on-time of the signal output during the time-bin slice for that electrode.

Referring to FIG. 6, another example of a feedback control method is illustrated schematically. The cyclical time slices for the electrodes is shown on the horizontal axis, and the signal output level on the vertical axis as in the FIG. 5. In this example, during a given time slice sequence such as, for example, the group of slices T1, T2, and T3, the level is held by the dependent controllers for the electrodes at VV1. During time slice T1, the duty time of the output can be controlled by the controller to be a fraction of the slice time T1, as illustrated by the time D1. Time duration D1 is controlled so that the temperature of the electrode 145 is steered back, by a feedback algorithm in the controller for electrode 145, to the set temperature value. Similarly, in the next group of time cycles are T4, T5, and T6. During the time slice T4 in which the electrode 145 is active, the dwell time of the signal output to the electrode 145 is D4. In T7, it is D7, and so on. The level at each group of time cycles can be changed as illustrated in FIG. 6 by the levels VV1, VV2, VV3, and so on. The level that is maintained and applied at each group of time cycles, can be determined by the feedback algorithm so that each and all of the electrodes can get the sufficient power of signal output during its allotted time slice to achieve the temperature of the set temperature. This can be done by the dependent coupling of the controllers, as, for example, indicate by the coupling lines 170 and 174 shown in FIG. 3.

Figure 7:
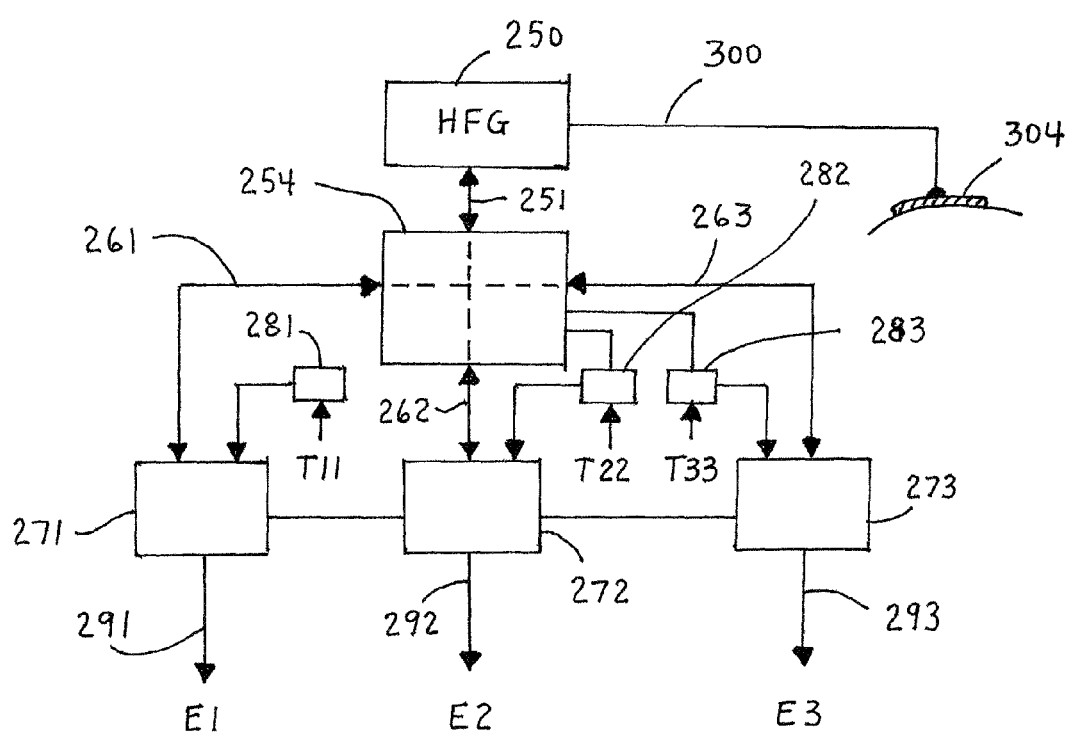
FIG. 7 shows a schematic block diagram of an electrical circuit comprising a master timing and coordinating controller that the controls the individual feed-back controllers of the individual electrodes.

Referring to FIG. 7, a schematic block diagram of circuit elements are shown that can dependently couple the controls for multiple electrodes E1, E2, E3 that can be connected to a high frequency generator 250. High frequency generator 250 is connected by connection 251 to a master controller 254, which controls the distribution of the signal output of 250 to the secondary controllers 271, 272, and 273. The secondary controllers, in turn, send the activation signal to the electrodes E1, E2, and E3, respectively. In one example, controller 254 comprises a master clock that determines the group cycle times, the time slices within the group cycle times, the signal output levels during each time slice, and/or the dwell times within each time slice corresponding to the electrode activations by the signal output from 250. This master control information is sent to the controllers 271, 272, and 273 by the connections 261, 262, and 263. In one example, the temperature signals from the electrode temperature sensors within the electrodes E1, E2, E3 are inputted, as illustrated by T11, T22, and T33, into set temperature controllers 281 282, and 283, respectively, which then send their signals to the controllers 271, 272, and 273, respectively, for secondary control of signal output levels and/or dwell times during each electrode time slice. This can enable the controllers to maintain a desired set temperature for each electrode. Also, in one example, the connections 261, 262, and 263 can comprise transport of an information signal back to the master controller 254 (indicated by the two-way arrow heads on these connections), based on the measured temperature, the set temperature, and the time slice parameters, so that master controller 254 can set the overall signal output level from the high frequency supply 250. This flow of information and control from 254 to 250 is schematically illustrated by the two-way arrow heads on the connection 251.

Referring to FIG. 7, a connection 300 is shown to a reference electrode 304. Reference electrode 304 can for example, be a grounding plate or pad that is connection to the patient's body skin to act as a return current path for the output of the high frequency generator. This is a common type of connection. In another example, the electrode E1, E2, E3, and more if the clinical need warrants it, can include reference electrode such as electrode 304, so that the system is then connected in multiple bipolar manner. The reference electrode can be of the same type as high frequency element normally inserted into the patient's body for RF lesioning, so that the reference electrode themselves become part of the therapeutic system, rather than being merely a passive return path for high frequency current.

Figure 8:
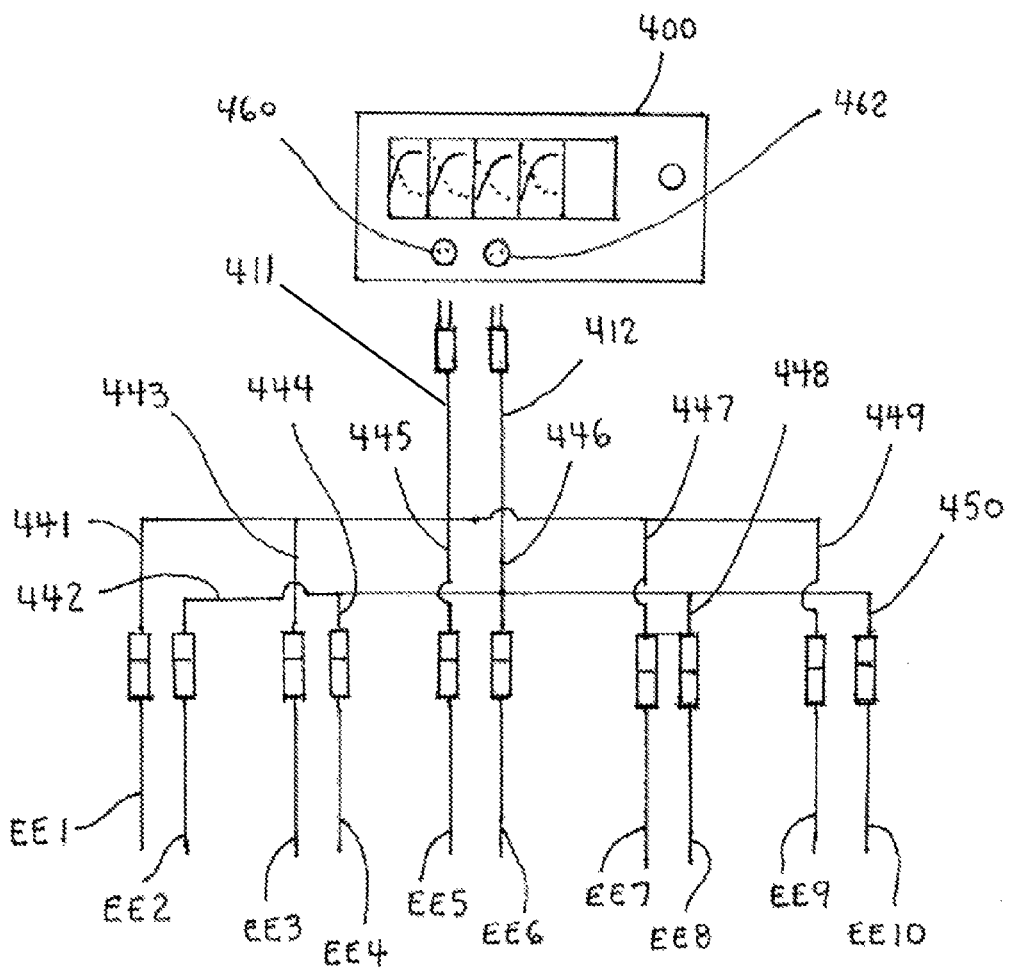
FIG. 8 shows a schematic diagram of a multi-electrode high frequency electrode system comprising multiple pairs of bipolar electrodes.

Referring to FIG. 8, a system of multiple electrodes connected to a high frequency generator is shown wherein the electrodes are configured in a multiple bipolar manner. In one example, the multi-bipolar signal outputs from generator 400 are sent out of jacks 460 and 462, each jack having multiple pin outputs that can send non-simultaneously cyclical signal outputs to multiple pin combinations. The cables 411 and 412 carry these signal outputs through multiple internal cables (not shown in the figure), and have a multiplicity of continuation cables, such as 441, 443, 445, 447, and 449 from line 411; and 442, 444, 446, 448, and 445 from line 412. These continuation cables, in turn, connect to the electrodes EE1, EE3, EE5, EE7, and EE9 for the continuation lines fanning from 411, respectively; and electrodes EE2, EE4, EE6, EE8 and EE10 from the continuation lines sited from cable 412, respectively. In one example, the pairs of bipolar electrodes, for example, EE1 and EE2 are activated as a bipolar pair, and the high frequency generator with its internal, non-simultaneous control functions, as described in connection with the previous figures, can activate these bipolar pairs to hold a desired set temperatures on them or to maintain them at a specific signal output level. Another time slice would apply to the bipolar pair EE2 and EE3 with their respective time slice and non-simultaneous activation and controls, and so on for all the bipolar pairs involved.

Referring to FIG. 8, in another example, the output lines 411 and 412 from the high frequency generate 400 can each carry a single high frequency bipolar signal that is connected directly though the connection lines 441, 443, 445, 447, and 449 for connection 411; and 442, 444, 446, 448, and 450 through the connection 412, respectively. In one example, the opposite polarity of the high frequency signal output from generator 400 would be connected to each of the respective pairs in the bipolar collection. For example, EE1, EE3, EE5, EE7 and EE9 would carry the plus signal output level, and EE2, EE4, EE6, EE8, EE10 would all carry the minus signal output value level. Thus the cabling connection structure comprising 411, 412 in combination with 441 through 450 can be a unitized cable system for delivering bipolar signal outputs to multiple electrodes in a bipolar RF system. This can have application when delivering, for example, pulsed RF signals to multiple bipolar electrode pairs.

Figure 9:
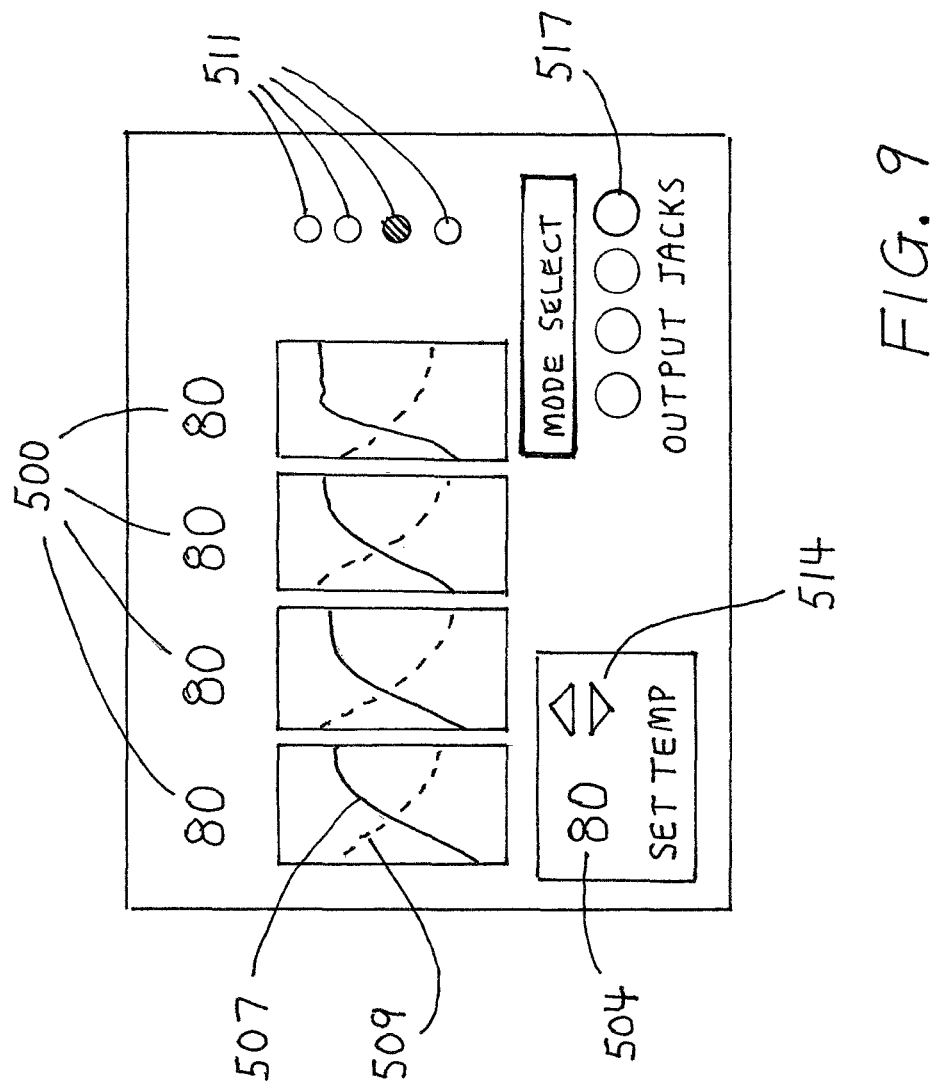
FIG. 9 is a schematic diagram showing a high frequency generator with four electrodes connected to it and graphic display.

Referring to FIG. 9, in one example, an embodiment of the user interface is illustrated. Displays 500 are digital indicators of electrode temperatures and/or other pertinent parameters or readouts associated with the multiple electrodes that can be connected to the system. In one example, they can be displayed in separate displays, and in another example, they can be displayed as part of a two dimensional screen display, and the design choice can be dependent on clinical or ergonomic needs. Digital displays of such parameters or readouts can, for example, be represented by LED or LCD digits. Element 507 represents a two-dimensional graphics display, and in FIG. 9 is displaying a graph of temperature from electrode measurements. The dashed curve 509 can represent the time course of another parameter, for example, voltage, current, and/or power delivered on-time the electrode(s). The panel 514 can be the automatic temperature control panel. The set temperature can be actuated up and down by the toggle switch, and the set temperature can be displayed digitally as, for example, 80. The displays or selector controls, indicated by the element 511, can be lights that indicate which of the multiple electrodes that the clinician wished to the active in the procedure, or they can be buttons that enable the clinician to select which of the multiple electrodes he wishes to be activated during the procedure. The present system and method is not restricted to graphics display, but can comprising other readout or display method and systems, including printout and hard copy devices. For example, other options for user interface can comprise the mode selector that can be represented by a series of buttons that are associated with indicator lights identified as 511. The electrode outputs are schematically shown as elements 517 which, for example, can be electrode jacks. The elements 517 can be the output jacks that enable connection to cable s that run to the electrodes.

Figure 10:
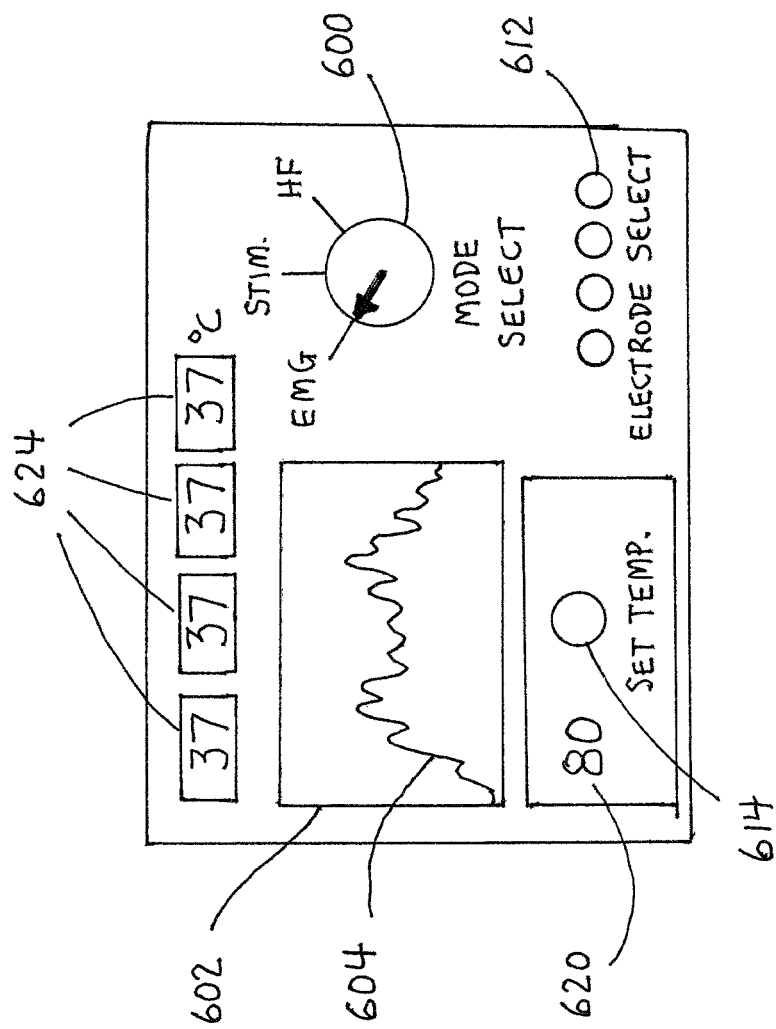
FIG. 10 is a schematic diagram showing a high frequency generator with EMG graphic display and multi electrode connections.

Referring to FIG. 10, in one example, the system is shown wherein the mode selector 600 has a position for EMG or EEG recording in addition to a stimulation position and a high frequency signal output delivery position. On the two-dimensional display 602, an EMG or EEG signal 604 can be represented as a graph 604 of EMG or EEG activity or of EMG/EEG activation signals, thus identifying electrophysiological activity of a nerve before and/or after the high frequency treatment. In one example, the elements 612 indicate the electrode output jacks. In the example shown, there are four electrode output jacks; however any number of electrodes greater than one is included within the scope of the present system and method. In one example, the Set Temp user interface can comprise a knob 614, however there are other implementations of this control that are possible, such as up/down switches, slide controls, and so on. Element 620 indicates the set temperature. Displays 624 can indicate the temperature readout values from the electrodes' temperature sensors, and in the FIG. 10, for example, they are all showing reading body temperature of 37 degrees which is typically the case before high frequency signal output is applied to the electrodes.

Figure 11:
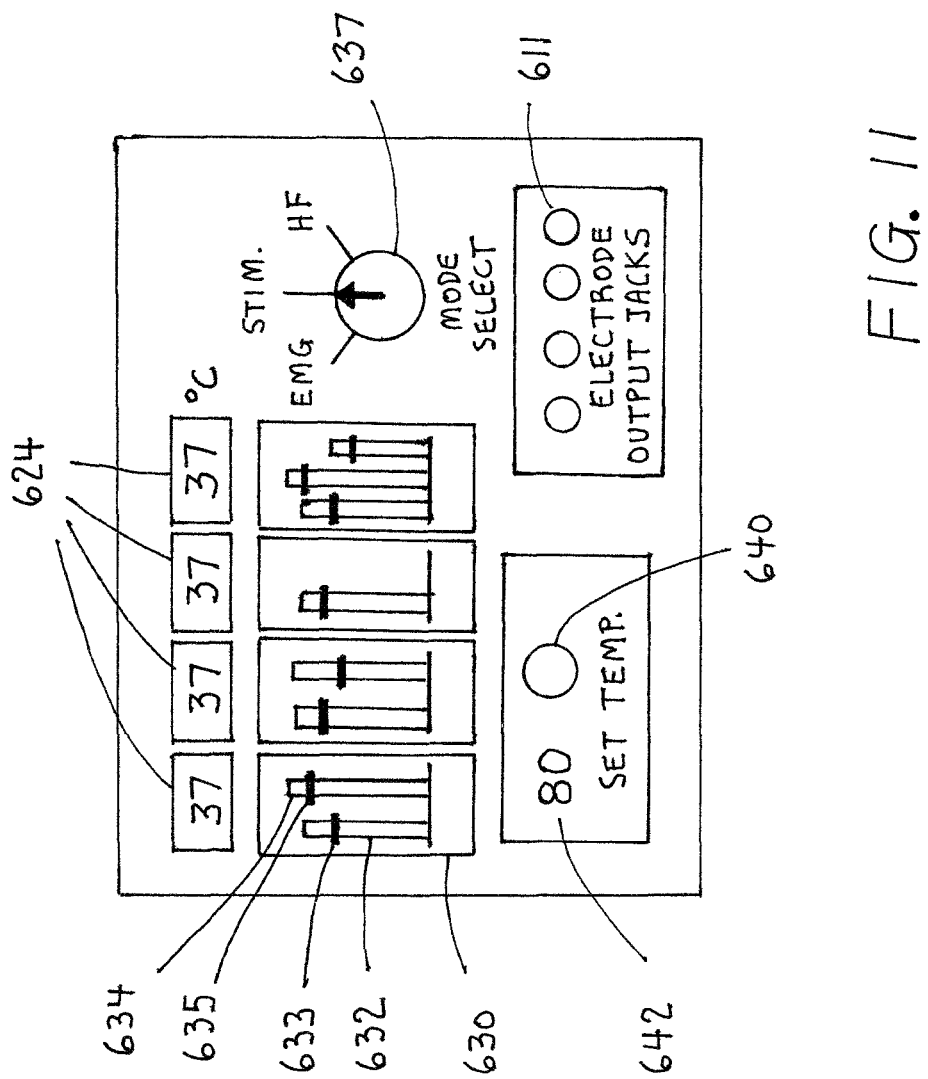
FIG. 11 is a schematic diagram showing a high frequency generator with four electrodes connections, graphic display, and recording of stimulation testing thresholds.

Referring to FIG. 11, a schematic representation of the system is shown. The mode selector 637 is in the stimulation position. A sensory stimulation graph 630 is displayed. In one example, the graphs for the stimulation levels can be shown for four electrodes. Typically, the stimulation signal output level, for example, voltage, is applied to each electrode independently and individually, so that the correct position of the electrode tip can be confirmed on the correct nerve. Each electrode that is connected to the system and is to be activated has associated with it a histogram such as 632 indicating, for example, stimulation sensory thresholds prior to making a heat or a pulsed high frequency lesion. This can be done for each electrode separately. There are many possible ways that these stimulation parameters can be represented. For example, FIG. 11 illustrates one example of the many such ways in which to achieve a representation of these stimulation parameters identifiable to the user. The small line 633 can indicate a level that the clinician has selected for that electrode position and can show for later record what was achieved. After the heat high frequency lesion, another stimulation testing can be done for the same electrode, and this can be shown as another histogram bar graph, for example line 634 together with a record index level marker 635. Similar bar graphs can be developed and displayed for the other electrodes, as is illustrated in the FIG. 11. The mode select switch, identified as 637, has settings for both delivery of high frequency signal output and for stimulation signal output. The displays 624 represent the temperature readouts measured at the electrodes. Typically, when stimulation is being delivered to the electrodes, there is no high frequency heating of the electrodes, so that the temperature readings 624 for the multiple electrodes would indicate body temperature of 37 degrees. The electrode outputs, represented by 612, can indicate connections to four electrodes, although any number of electrodes greater than one is anticipated in this present system and method. Set temperature can be adjusted by knob 640, and an example of a set temperature displayed value is represented by display 642.

Figure 12:
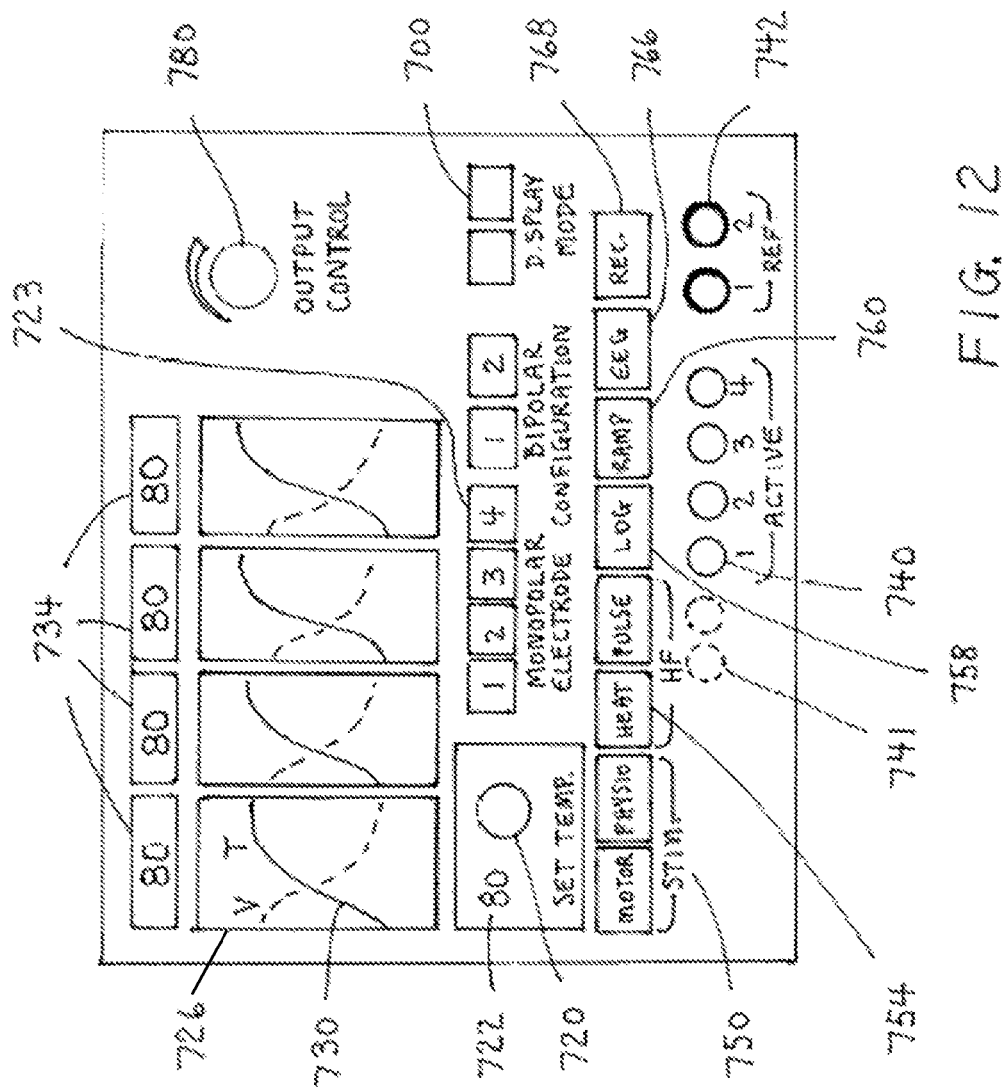
FIG. 12 is a schematic diagram showing a high frequency generate with multi-electrode connections, graphic display, and flexible mode selection buttons.

Referring to FIG. 12, in one example, another user interface is shown. A mode select button, 700, can allow the user to select between EMG/EEG, HF, and stimulate modes. In one example, the modes of: stimulation 750, high frequency output modes 754, recording LOG 758, RAMP of the high frequency output increase 760, EEG or EMG recording 766, and recording of the parameters used 768, are actuated by push buttons. When the stimulation or the EMG mode is selected, digital display(s) or pushbuttons The electrode mode or configurations used can be represented by other pushbuttons, for example, 723, which can indicate which electrode is selected. Integral he electrode modes, the user can select one electrode at time for EMG/EEG or stimulation activation. The system enables the user to know which of the multiple possible electrodes that are being considered is being connected at any given time to the EMG/EEG or to the stimulation output mode, on-time for the high frequency treatment. The electrode selection can be made by the knob or pushbutton as illustrated by element 723. In one example, the user set temperature is identified as a knob indicated by 720, and the set temperature value is represented by 722, and this display, in one example, is incorporated within a two-dimensional graphics display 726. A time versus temperature graph is indicated by 730 for the individual electrodes, if high frequency signal output mode is selected on the mode select, is indicated by 754. Display 740, in the example, is in FIG. 12, indicative of four electrode outputs. Dotted circles 741 represent that more than four electrodes or less than four electrodes can be used, according to clinical needs.

Figure 13:
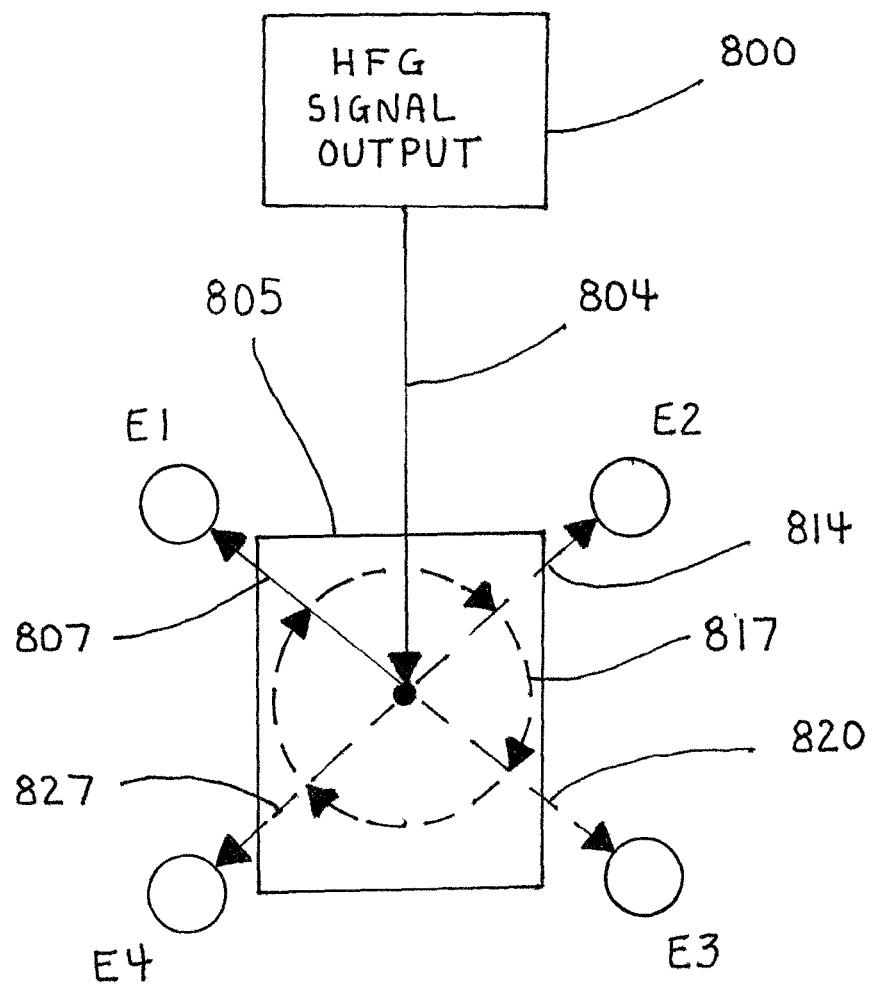
FIG. 13 is a schematic diagram showing a block diagram of circuit elements for cyclical non-simultaneous sequencing to a four electrodes.

Referring to FIG. 13, a schematic diagram of the sequential flow of high frequency signal output to four electrodes is shown. The signal output from high frequency generator 800 is distributed in a timing cycle through the control element 805 which distributes the signal output as indicated schematically by the rotary arrow 807. 807 is symbolically a 'phasor' showing that the output can first be connected to electrode E1, as shown by the solid arrow 807, and then as time progresses, it is connected to E2, indicated by the dashed arrow 814. The rotor distributor or 'phasor' 807 continues in a schematically indicated dashed clockwise circle 817 representative of the passage of time, so that it connects in turn with E3 indicated by dashed arrow 820, and E4 indicated by arrow 827, and continues on around the cycle to repeat its connection automatically to the four electrodes again and again during the procedure duration. This can be referred to as 'cyclodromic' distribution control of the high frequency signal output to multiple electrodes. The contact to any electrode is non-simultaneous to the contact with any other electrode, so the process can be said to be non-simultaneously cyclodromic.

Figure 14:
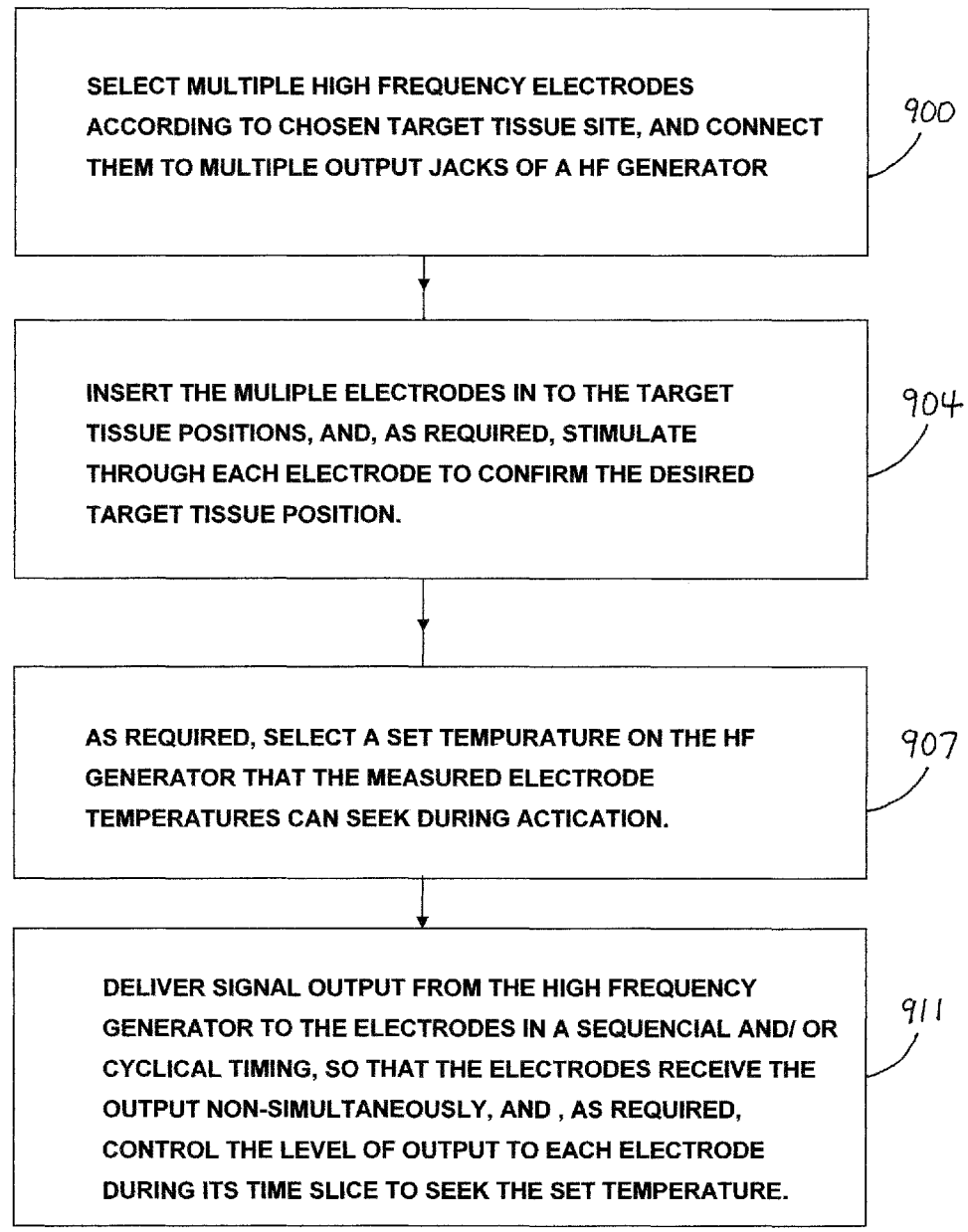
FIG. 14 is a schematic flow diagram for non-simultaneous sequencing of generator output to multiple electrodes.

Referring to FIG. 14, a flow diagram shows schematically a process for the method of the present invention, Step 900 comprises the selection of multiple electrodes to be used according to clinical needs. Step 900 can include the decision on how many electrodes are needed to fulfill clinical objectives the procedure. In one example, the electrodes can be chosen to make heat lesions at multiple levels of the spine or the medial branches of the spinal segmental nerves. In step 900, the electrodes can be connected by cables to the high frequency generator. In step 904, the electrodes are positioned in the patient's body so that their tips are at the desired target tissue sites. Step 904 can, for example, include the steps of stimulation-testing using the motor and/or physiological stimulation signal output levels and pulse frequencies that can be user-selected from the system, applied at each electrode individually. In this way, the appropriate positioning of the individual electrode tips can be confirmed at the correct position with respect to the target nerves. In step 907, the desired set temperature can be selected on the interface of the high frequency generator. In one example, the set temperature can be the same for all of the electrodes, and, in another example, the set temperature can be different for the electrodes, this choice can be made by the clinician according to his clinical needs. In step 911, the clinician can select the number of multiple electrodes that he desires to activate for the clinical procedure. The activation of the system can initiate a sequential and/or cyclical delivery of the high frequency signal output from the system to the multiple electrodes in such a way that the signal output is applied in a non-simultaneous time sequence. This can proceed by automatically delivering the high frequency output to one electrode at a time corresponding to that electrode's programmed time slice, and according to a controlled sequence of time slices for the multiple electrodes, as has been illustrated in the FIGS. 1 through 13. Step 911 can involve varying the dwell time and/or the amplitude of the high frequency output to each electrode during its time slice to maintain set a parameter value, such as set temperature, as described in FIGS. 1-13.

The system and method described herein can be used in a variety of medical applications. In one example, it can be used to treat neural tissue in the brain, spine, or peripheral anatomy to manage pain, mood disorders, or movement disorders such as Parkinson's disease. In another example, it can be used to treat cancerous tumors anywhere in the patient's body. It can be to treat many various target tissue sites and disease states, as can be considered by clinicians and others skilled in the medical art.

A number of embodiments of the invention have been described. Nevertheless, it will be understood that various modifications may be made without departing from the spirit and scope of the invention. Accordingly, other embodiments are within the scope of the followings Claims:

The invention claimed is:

1. An apparatus for performing tissue modification procedures on a patient's body, comprising:
a high frequency generator configured to automatically deliver non-simultaneously a high frequency signal output to an at least two electrodes in a cyclical sequence so that no two electrodes have said high-frequency signal output applied to them at the same time, wherein a temperature sensor is incorporated into a tip portion of each electrode;
an individual set temperature controller for each of said electrodes, wherein each said individual set temperature controller continuously monitors the temperature at its corresponding electrode relative to an individual set temperature for that electrode to produce a temperature-control signal for that electrode;
an individual secondary controller for each said electrode that is configured to connect and disconnect that electrode from said high-frequency signal output; and
a master controller that processes the temperature-control signals for all electrodes to adjust for each cycle of said cyclic sequence both the signal output level of said high-frequency signal output and the timing with which said secondary controllers apply said high-frequency signal output to their respective electrodes, in order to maintain the temperature of each said electrode at its respective set temperature, wherein the master controller is programmed to divide each cycle into a plurality of time bins and to control the secondary controllers such that only one electrode is activated during each successive time bin.

2. The apparatus in accordance with claim 1, wherein each of the at least two electrodes is at least partially electrically insulated over at least part of a shaft of said electrode.

3. The apparatus in accordance with claim 1, further comprising a user interface configured to allow a user to set to the desired temperature of each or all electrodes.

4. The apparatus in accordance with claim 3, wherein the user interface further comprises at least one display configured to display a graphic representation of a temperature of each electrode tip, and/or a time versus temperature of each of the electrodes.

5. The apparatus in accordance with claim 4, wherein said user interface can also display EMG and/or EEG signals that are recorded from each of said electrodes.

6. The apparatus in accordance with claim 5, wherein the user interface is also configured to deliver audible representations of the EMG and/or EEG signals.

7. The apparatus in accordance with claim 4, wherein the user interface is also configured to record and display user selectable sensory stimulation thresholds for each of the electrodes.

8. The apparatus in accordance with claim 1, wherein the high frequency generator is configured to deliver low frequency (1-1000 Hz) stimulation pulses.

9. The apparatus in accordance with claim 1, wherein the generator is configured to deliver programmatically the high frequency signal output to each of said electrodes.

10. The apparatus in accordance with claim 1, wherein the generator is configured to deliver sequentially the high frequency signal output to each of said electrodes.

11. The apparatus in accordance with claim 1, wherein the signal output level is a voltage, current, or power.

12. The apparatus in accordance with claim 1, wherein each individual set temperature is independently selectable for each said electrode.

13. The apparatus in accordance with claim 1, wherein each said cycle is divided evenly into time slices, wherein in each time slice, the high-frequency signal output can be applied to only one said electrode, and wherein fractional time of application of high-frequency signal output to each said electrode is regulated by varying the duration over which high-frequency signal output is applied that electrode within its corresponding time slice.

14. The apparatus in accordance with claim 1, wherein fractional time of delivery of high-frequency signal output to each said electrode is regulated by varying a duration over which said high-frequency signal output is applied to that electrode within each said cycle.

15. The apparatus in accordance with claim 1, wherein each individual set temperatures is the same and selectable by a single scalar parameter.

16. The apparatus in accordance with claim 1, wherein the master controller holds said signal output level of said high-frequency signal output at a constant value for the duration of each cycle of said cyclic sequence.

17. The apparatus of claim 1 wherein at least two of the electrodes are configured for mechanically-independent insertion into the patient's body.

18. The apparatus of claim 1 adapted to be able to heat and maintain the temperature of each electrode at a temperature value between 45° C. and 100° C.

19. The apparatus of claim 1 and further including a reference electrode, wherein the high frequency signal output includes high frequency electrical current that flows through the patient's body from each electrode to the reference electrode.

20. The apparatus of claim 19 wherein the reference electrode is a ground pad placed on the surface of the patient's body.

21. A system for performing tissue modification procedures on a patient's body, comprising:
a high-frequency generator configured to deliver a high frequency signal output, coupled to at least two connection jacks configured to attach to at least two non-connected separate electrodes in a cyclical sequence so that no two electrodes have said high-frequency signal, output applied to them at the same time, wherein one of the at least two connection jacks connects to one of the at least two electrodes, wherein each electrode includes a temperature sensor in a tip portion of the electrode, the temperature sensor being configured to measure a temperature of the tip portion of the electrode; and
an automatic controller system configured to automatically switch the delivery of the high-frequency signal output to each connection jack of the at least two connection jacks sequentially such that the high-frequency signal output is only delivered to one connection jack of the at least two connection jacks at a time;
wherein the automatic controller system includes a feedback control circuitry configured to maintain a set temperature at each of said electrodes by adjusting both the signal output level of said high-frequency signal output and a fractional time of application of said high-frequency signal output to each said electrodes based on continuous temperature measurements from said temperature sensors, and wherein said feedback control system is configured to apply the same signal output level to all electrodes during each cycle of said cyclical sequence of said automatic delivery of high-frequency signal output, wherein the automatic controller is programmed to divide each cycle into a plurality of time bins and to control energy delivery to each of the connection jacks such that only one electrode is activated during each successive time bin.

22. The system of claim 21, wherein the automatic controller system further includes at least two controllers logically connected to each other and at least two switches, each connection jack being coupled to the high frequency generator via a switch, such that when a switch is in a closed position the high frequency generator can deliver a high frequency signal output to the connection jack via the closed switch and when a switch is in an open position the high frequency generator cannot deliver a high frequency signal output to the connection jack via the open switch, each controller controlling whether the switch is in the open or closed position, wherein only one switch can be closed at any given point in time.

23. The system of claim 21, further comprising a user interface configured to allow a user to select a desired temperature individually for each electrode and the user interface is configured to select a mode of operation from a plurality of modes of operation, the plurality of modes of operation including an automatic multiple output mode in which the automatic controller is activated.

24. The system of claim 23, wherein the user interface is configured to allow a user to select the same desired temperature for each electrode of the at least two electrodes.

25. The system of claim 23, wherein the user interface includes a temperature selection device and a mode selection device.

26. The system of claim 23, wherein the plurality of modes of operation further includes an individual output mode in which each connection jack of the at least two connection jacks is individually selected to receive a high-frequency signal output delivered from the high frequency generator, whereby the high-frequency signal output delivered to the connection jacks from the high frequency generator can be controlled either manually by a user control or automatically by the feedback control circuitry jacks such that a temperature of each electrode as measured by the temperature sensor is maintained at a desired temperature when the at least two electrodes are in contact with the patient's body.

27. The system of claim 21, further comprising a stimulation circuitry configured to deliver a stimulate output signal, and the plurality of modes of operation further including an individual stimulation mode in which each connection jack of the at least two connection jacks is individually selected to receive the stimulator output signal delivered from the stimulation circuitry, a level of the stimulator output signal to each electrode of the at least two electrodes via a connection jack can be controlled to enable stimulation threshold testing when an electrode connected to the selected connection jack is in contact with the patient's body.

28. The system of claim 21, wherein the at least two electrodes each comprise an elongated electrode shaft configured to be inserted into a tissue of the patient's body, and the elongated electrode shaft has at least a portion of its surface that is uninsulated and conductive such that when the high-frequency signal output is delivered to each electrode, the signal output energizes the tissue of the patient's body near the uninsulated conductive portion to produce heating of the tissue near the uninsulated conductive portion.

29. The system of claim 21, further comprising a graphics display adapted to display the measured temperatures of each electrode continuously and simultaneously in time.

30. A system for performing tissue modification procedures on a patient's body, comprising:
a high-frequency generator configured to deliver a high frequency signal output, coupled to at least two connection jacks, which are configured to attach to at least two non-connected separate electrodes in a cyclical sequence so that no two electrodes have said high-frequency signal output applied to them at the same time, wherein one of the at least two connection jacks connects to one of the at least two electrodes, wherein each electrode includes a temperature sensor in a tip portion of the electrode, the temperature sensor being configured to measure a temperature of the tip portion of the electrode; and
an individual set temperature controller for each of said electrode, wherein each said individual set temperature controller continuously monitors the temperature at its corresponding electrode relative to an individual set temperature for that electrode to produce a temperature-control signal for that electrode;

an individual secondary controller for each said electrode that is configured to connect and disconnect that electrode from said high-frequency signal output; and a master controller that processes the temperature-control signals for all electrodes to adjust for each cycle of said cyclic sequence both the signal output level of said high-frequency signal output and the timing with which said secondary controllers apply said high-frequency signal output to their respective electrodes, in order to maintain the temperature of each said electrode at its respective set temperature, wherein the master controller is programmed to divide each cycle into a plurality of time bins and to control the secondary controllers such that only one electrode is activated during each successive time bin.

31. The system of claim 30, further comprising a user interface configured to allow a user to select a desired temperature individually for each electrode and the user interface is configured to select a mode of operation from a plurality of modes of operation, the plurality of modes of operation including an automatic multiple output mode in which the automatic controller is activated.

32. The system of claim 31, wherein the plurality of modes of operation further includes an individual output mode in which each connection jack of the at least two connection jacks is individually selected to receive a high-frequency signal output delivered from the high frequency generator, whereby the high-frequency signal output delivered to the connection jacks from the high frequency generator can be controlled either manually by a user control or automatically by the feedback control circuitry jacks such that a temperature of each electrode as measured by the temperature sensor is maintained at a desired temperature when the at least two electrodes are in contact with the patient's body.

33. The system of claim 31, wherein the user interface is configured to allow a user to select the same desired temperature for each electrode of the at least two electrodes.

34. The system of claim 30, wherein the master controller controls a level of the high frequency signal output and/or a dwell time of the high frequency output signal that is delivered to the one connection jack which corresponds to each time slice such that a temperature of each electrode as measured by the temperature sensor is maintained at a desired temperature.

35. The system of claim 30, wherein the at least two electrodes each comprise an elongated electrode shaft configured to be inserted into a tissue of the patient's body, and the elongated electrode shaft has at least a portion of its surface that is uninsulated and conductive such that when the high-frequency signal output is delivered to each electrode, the signal output energizes the tissue of the patient's body near the uninsulated conductive portion to produce heating of the tissue near the uninsulated conductive portion.

36. The system of claim 30, further comprising a stimulation circuitry configured to deliver a stimulate output signal, and the plurality of modes of operation further including an individual stimulation mode in which each connection jack of the at least two connection jacks is individually selected to receive the stimulator output signal delivered from the stimulation circuitry, a level of the stimulator output signal to each electrode of the at least two electrodes via a connection jack can be controlled to enable stimulation threshold testing when an electrode connected to the selected connection jack is in contact with the patient's body.

37. The apparatus in accordance with claim 30, wherein the master controller holds said signal output level of said high-frequency signal output at a constant value for the duration of each cycle of said cyclic sequence.

38. An apparatus for performing tissue modification procedures on a patient's body, comprising:

a high frequency generator configured to automatically deliver a high-frequency signal output non-simultaneously to an at least two electrodes, wherein a temperature sensor is incorporated into a tip portion of each electrode to measure the temperature at that electrode;

a set temperature for each said electrode;

individual set temperature controllers that continuously and individually monitor the temperatures at the electrodes relative to their respective said set temperatures;

a master controller that controls the distribution of said high-frequency signal output to said electrodes in a cyclic sequence of groups of times slices, that sets the same signal output level of the high-frequency signal output for each said group of time slices, and that sets a duty time during each said time slice, wherein the master controller is programmed such that in a given time slice only one electrode is allowed to be connected to the high-frequency signal output, wherein a group of time slices is a sequence of non-overlapping said time slices in which there is at least one said time slice for each said electrode, and wherein the duty time during each said time slice is the amount of time within that time slice for which the corresponding said electrode is connected to the high-frequency signal output;

individual secondary controllers that distribute the high-frequency signal output to the electrodes individually, wherein an individual secondary controller is configured to connect an electrode to the high-frequency signal output during the duty time of each said time slice for that electrode, and to disconnect that electrode from said high-frequency signal output at all other times;

a feedback controller having a feedback algorithm that analyzes the control signals produced by the individual set temperature controllers in order to adjust the output level of the high-frequency signal output for each said group of time slice, and to adjust the duty time during a time slice of each electrode for each said group of times slices, wherein said adjustments are configured to modify delivery of said high-frequency signal output to each said electrode so that the temperature at that electrode is driven toward the set temperature for that electrode.

* * * * *